United States Patent [19]

Chang

[11] Patent Number: 5,808,017
[45] Date of Patent: Sep. 15, 1998

[54] PROCESS FOR PREPARING ERYTHROMYCIN A OXIME

[75] Inventor: Sou-Jen Chang, Grayslake, Ill.

[73] Assignee: Abbott Laboratories, Abbott Park, Ill.

[21] Appl. No.: 630,306

[22] Filed: Apr. 10, 1996

[51] Int. Cl.⁶ ...................................................... C07H 1/00
[52] U.S. Cl. ............................................. 536/7.4; 536/18.5
[58] Field of Search ............................... 536/7.2, 7.4, 18.5

[56] References Cited

U.S. PATENT DOCUMENTS

| | | | |
|---|---|---|---|
| 3,478,014 | 11/1969 | Djokic et al. | 536/7.2 |
| 4,150,220 | 4/1979 | Sciavolino | 536/7.2 |
| 4,526,889 | 7/1985 | Bright | 514/29 |
| 4,672,109 | 6/1987 | Watanabe et al. | 536/7.2 |
| 5,274,085 | 12/1993 | Amano et al. | 536/7.4 |

OTHER PUBLICATIONS

*Tetrahedron Letters*, vol. 2 (1970), pp. 157–160, E. H. Massey et al., "Erythromycylamine".

*Primary Examiner*—Elli Peselev
*Attorney, Agent, or Firm*—Mona Anand; Thomas D. Brainard

[57] ABSTRACT

A process of preparing 9-oxime erythromycin A using a mild acid catalyst such as acetic acid and a mildly polar solvent such as isopropanol is provided. In accordance with that process, erythromycin A is reacted with hydroxylamine in the presence of acetic acid and isopropanol. A process of the present invention can also be used to increase the E to Z isomeric ratio of synthesized 9-oxime erythromycin A.

5 Claims, No Drawings

PROCESS FOR PREPARING ERYTHROMYCIN A OXIME

TECHNICAL FIELD OF THE INVENTION

The field of the present invention is erythromycin A 9-oxime production. More particularly the present invention pertains to the production of 9-oxime erythromycin A using a mildly polar solvent and a mild acid catalyst.

BACKGROUND OF THE INVENTION

6-O-methylerythromycin A (clarithromycin), shown below, is a potent macrolide antibiotic (U.S. Pat. No. 4,331,803).

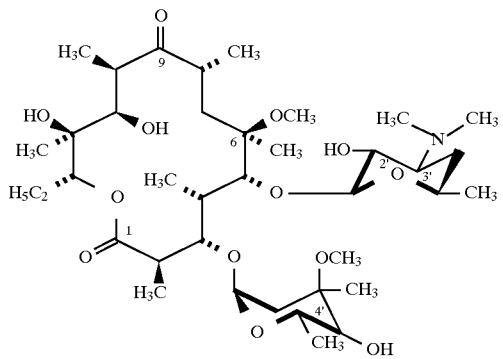

Clarithromycin

A variety of processes for preparing 6-O-methylerythromycin A have been described. By way of example, 6-O-methylerythromycin A can be made from 9-oxime erythromycin A derivatives (See, e.g., U.S. Pat. Nos. 5,274,085; 4,680386; 4,668776; 4,670,549, 3,478,014 and 4,672,109 and European Patent Application 0260938 A2, the disclosures of which are all incorporated herein by reference). The 9-oxime erythromycin A derivative can be made by reacting erythromycin A with either hydroxylamine hydrochloride and a base (See, e.g., U.S. Pat. No. 3,478,014, the disclosure of which is incorporated herein by reference) or free hydroxylamine in methanol and an organic acid (See, e.g., U.S. Pat. No. 5,274,085, the disclosure of which is incorporated herein by reference).

A 9-oxime erythromycin derivative can exist in either of two isomeric forms relative to the 9-oxime moiety. Where the 9-oxime is in the trans position (9-trans-oxime), the isomer is referred to as the E-isomer. A 9-cis-oxime erythromycin is known as the Z-isomer. As is well known in the art, the E isomer is the only active species for the synthesis of macrolide antibiotics using 9-oxime erythromycin as a starting material.

The use of methanol and an organic acid to prepare 9-oxime erythromycin derivatives is associated with certain problems. By way of example, use of those reactants typically results in the production of substantial amounts of the inactive Z-isomer and substantial amounts of degradation impurities. Both of these problems necessitate the use of time consuming and costly procedures to purify the E-isomer for subsequent reactions in antibiotic synthesis.

There continues to be a need in the art, therefore, for a method of making 9-oxime erythromycin derivatives that minimizes the formation of inactive isomers and degradation impurities while maintaining a high production yield.

BRIEF SUMMARY OF THE INVENTION

The present invention provides a new and improved process of preparing 9-oxime erythromycin A using a mild acid catalyst in combination with a mildly polar solvent. In accordance with the present process, erythromycin A, dissolved in the solvent, is reacted with hydroxylamine in the presence of the mild acid catalyst. Suitable mildly polar solvents are isopropanol and ethanol; whereas methanol does not appear to be suitable. Suitable mild acid catalysts are acetic or formic acid. In one embodiment, aqueous hydroxylamine is first added to a solution of erythromycin A in the solvent to form a reaction mixture and then the mild acid catalyst is added to the reaction mixture. In another embodiment, aqueous hydroxylamine is first mixed with the acid catalyst to form a mixture and the mixture is then added to a solution of erythromycin A in solvent.

Advantages of the process of the present invention include a significant improvement in yield, ease of liquid reagent handling and the ready availability of the starting materials, reagents and solvents. The use of mild acid catalysts and isopropanol also results in a homogenous reaction mixture that contains relatively few degradation impurities and, thus, allows for the direct recycling of the process solvents into subsequent stages of antibiotic (e.g., clarithromycin) synthesis.

It will be appreciated that the invention may also be practiced with erythromycin derivatives other than erythromycin A that also require temporary protection of the 9-oxo function prior to a subsequent reaction.

In another aspect, the present invention provides a process of increasing the E to Z isomeric ratio of 9-oxime erythromycin A. In accordance with that process, erythromycin A is reacted with hydroxylamine in the presence of isopropanol and a mild acid catalyst. Preferred catalysts and reaction conditions are the same as set forth above.

DETAILED DESCRIPTION OF THE INVENTION

The preparation of 9-oxime erythromycin A begins with erythromycin A, which is dissolved in a mildly polar solvent. An aqueous solution of hydroxylamine is added to the erythromycin solution to form a reaction mixture. A mild acid catalyst is then added to the reaction mixture. Mildly polar solvents suitable for use in a process of the present invention include ethanol and isopropanol, but not methanol. Suitable mild acid catalysts include acetic acid and formic acid.

The exact proportions of the reactants is readily ascertainable by a skilled artisan. Typically, the weight ratio of hydroxylamine to erythromycin A is from about 0.5 to 1.5:1. Preferably, about equal amounts of hydroxylamine and erythromycin A are used. As exemplified hereinafter, yields of 9-oxime erythromycin A greater than about 97.5% percent were obtained when 42.5 grams of hydroxylamine and 50 grams of erythromycin A were used in a process of the present invention. The hydroxylamine is preferably provided in the form of an aqueous solution containing from about 30 to about 70 percent by weight of hydroxylamine.

The erythromycin used in the process is dissolved or suspended in the mildly polar solvent. Typically, the weight to volume ratio of erythromycin A to solvent is from about 0.3 grams/ml to about 0.7 grams per ml. More preferably, about 0.5 grams of erythromycin A are dissolved in 1 ml of solvent. Catalytic amounts of the mild acid catalyst are used. Preferred amounts of acetic or formic acid are from about 0.25 grams to about 0.5 grams of catalyst per gram of erythromycin.

After addition of all the reactants, the reaction solution is heated at a temperature of from about 35° C. to about 65° C.

until the reaction is complete. A more preferred temperature is from about 45° C. to about 55° C. The solution is then cooled to room temperature. An isopropyl salt of the acid catalyst (e.g., isopropyl acetate or isopropyl formate) is added to the cooled solution and the pH of the solution is adjusted to a value of not less than 11.0 with a strong alkalai metal base such as sodium hydroxide. The organic layer can be concentrated to dryness to yield the formed 9-oxime erythromycin A.

The acid catalyst can be pre-mixed with the hydroxylamine free base prior to mixing it with erythromycin A. This allows for reduction of the heat generated upon erythromycin A addition. A process of the present invention improves the yield of 9-oxime erythromycin A. As set forth in detail hereinafter in the Examples, the use of isopropanol or ethanol with acetic acid resulted in 9-oxime yields of greater than 97.6%.

In another aspect, the present invention provides a process of preferentially synthesizing 9-trans-oxime erythromycin A (the E isomer) relative to 9-cis-oxime erythromycin A (the Z isomer). The process includes the steps of reacting erythromycin A with hydroxylamine in the presence of isopropanol and a mild acid catalyst. Preferred mild acid catalysts are the same as set forth above. As set forth in detail hereinafter in the Examples, the use of isopropanol and acetic or formic acid resulted in the formation of 9-oxime erythromycin A having an E/Z isomeric ratio of greater than 6.0.

The formed 9-oxime erythromycin A can be crystallized. Crystallization is accomplished by dissolving dried, crude 9-oxime erythromycin A, prepared as set forth above, in an appropriate solvent so as to form a homogeneous solution. A preferred solvent for crystallization is a mixture of isopropanol and water. Preferably, the ratio of isopropyl alcohol to water is from about 70:30 to about 90:10. The homogeneous solution is cooled to about room temperature and the formed crystals collected by filtration. The pure crystals are then dried using, for example, a vacuum oven.

9-Oxime erythromycin A prepared in accordance with a process of the present invention can then be used to prepare 6-O-alkylerythromycin A derivatives in accordance with standard procedures well known in the art. Those subsequent steps frequently include the steps of protecting the 2'-hydroxy group (with or without optional protection of the 3'-dimethylamine and 4"-hydroxy group), selective alkylation of the 6-hydroxy group, deprotection of the protected groups and deoximation. Those steps can be carried out by a variety of means known in the art (See, e.g., U.S. Pat. Nos. 5,274,085; 4,680,386; 4,668,776; 4,670,549 and 4,672,109 and European Patent Application 0260938 A2, the disclosures of which are incorporated herein by reference).

As is well known in the art, to efficiently and selectively alkylate erythromycin A at the 6-hydroxyl position using known methods, the hydroxyl group at the 2'- position should be O-protected prior to alkylation. O-protection of the 2'-hydroxyl is accomplished using conventional O-protecting groups (See, e.g., U.S. Pat. No. 4,672,109). Exemplary and preferred such O-protecting groups are alkoxycarbonyl groups; alkoxyalkoxycarbonyl groups; haloalkoxycarbonyl groups; unsaturated alkoxycarbonyl groups; substituted benzyloxycarbonyl groups; substituted phenoxycarbonyl groups; aroyl groups; acyl groups used in usual organic synthesis; lower alkenyl monocarbonyl groups; lower alkoxycarbonylalkylcarbonyl groups; and arylcarbonyl groups (See, e.g., Greene and Wuts' *Protective Groups in Organic Synthesis*, 2d. Ed. John Wiley & Sons, Inc., New York, 1991., the disclosure of which is incorporated herein by reference).

The 2-O-protected compound is then selectively alkylated, usually methylated, at the 6-position. Procedures and reagents for alkylating the 6-position of erythromycin A derivatives are well known in the art (See, e.g., U.S. Pat. Nos. 4,672,109 and 4,670,549, the disclosures of which are incorporated herein by reference). Briefly, a compound is reacted with a suitable alkylating agent in the presence of a base. Exemplary and preferred alkylating agents are methyl bromide, ethyl bromide, n-propyl bromide, methyl iodide, ethyl iodide, n-propyl bromide, dimethyl sulfate, diethyl sulfate, di-n-propyl sulfate, methyl-p-toluenesulfonate, ethyl methanesulfonate, and n-propyl methanesulfonate. Exemplary and preferred bases are a strong alkali metal base, preferably selected from the group consisting of an alkali metal hydride, alkali metal hydroxide or alkali metal alkoxide, and a weak organic amine base, preferably selected from the group consisting of trimethylamine, triethylamine, tripropylamine, pyridine, 2-methoxypyridine, 1-methylpyrrolidine, 1-methylpiperidine, and 1-ethylpiperidine.

A final step in the preparation of 6-O-alkylerythromycin A is deoximation. Deoximation is carried out in accordance with standard procedures well known in the art (See e.g., U.S. Pat. No. 4,672,109). Briefly, the 9-oxime derivative is reacted with sodium hydrogen sulfite in alcohol (e.g., ethanol) and refluxed. The solution is cooled, alkalinized and precipitated with aqueous sodium bicarbonate. The precipitate formed in the above reaction is collected by filtration, washed and recrystallized with alcohol.

The following Examples illustrate preferred embodiments of the present invention and are not intended to limit the invention, which is defined by the appended claims.

EXAMPLE 1

Production of 9-Oxime Erythromycin A

50% aqueous hydroxylamine (42.5 g.) was added to a stirred mixture of Erythromycin A (50 g) in isopropanol (100 ml). To this mixture acetic acid (16.3 g) was added. A clear solution was formed and heated at 50° C. until the completion of the reaction. At the end of the reaction, the mixture was cooled to room temperature, and isopropyl acetate (150 ml) was added. The mixture was vigorously stirred while 4N NaOH was added to adjust the pH to a value of no less than 11.0. The organic layer was washed with dilute caustic and concentrated to dryness to give Erythromycin A oxime. Alternatively, the organic layer was assayed to show a 98.9% yield.

In an alternate embodiment, 16.3 grams of acetic acid are added to a 50% aqueous hydroxylamine (42.5 g.). This solution is then added to a stirred mixture of Erythromycin A (50 g) in isopropanol (100 ml). Subsequent steps are performed as described above.

EXAMPLE 2

Comparison of the Use of Acetic Acid/Isopropanol with Other Acid/Solvent Systems 9-Oxime erythromycin A was prepared in accordance with the procedures of Example 1 except that various combinations of acids and alcohols were used in addition to acetic acid and isopropanol. Those other combinations included methanol (MeOH) with formic acid (HCOOH), isopropanol (IPA) with HCOOH, MeOH with acetic acid (HOAc), IPA with HOAc and ethanol (EtOH) with HOAc. The results of those studies are summarized below in Table 1.

TABLE 1

| Solvent | Acid Catalyst | % Yield | E/Z Ratio |
|---|---|---|---|
| MeOH | HCOOH | 90.7 | 4.59 |
| MeOH | HCOOH | 92.9 | 3.85 |
| IPA | HCOOH | 91.0 | 7.50 |
| IPA | HCOOH | 88.5 | 6.45 |
| MeOH | HOAc | 93.6 | 5.06 |
| IPA | HOAc | 99.0 | 6.44 |
| IPA | HOAc | 97.6 | 6.88 |
| IPA | HOAc | 99.5 | 7.37 |
| IPA | HOAc | 98.3 | 7.7 |
| EtOH | HOAc | 98.7 | 3.3 |

It can be seen from the data in Table 1 that the combination of isopropanol and acetic acid gave the optimum yields with highest E/Z isomer ratio.

EXAMPLE 3

Crystallization of Erythromycin A Oxime

Erythromycin A oxime as prepared in isopropanol/acetic acid was crystallized in various solvents to compare the purity, recovery, yield and ease of filtration (particle size). The results are summarized below in Table 2. 80/20 Isopropanol/water gave 75% yield of the oxime major isomer (E isomer) with 88.0% purity (based on the standard of 92.4% purity).

Crystallization of Erythromycin A Oxime

| Solvent | Wt % E Isomer | Wt % Z Isomer | E Isomer % Yield | E Isomer % Recovery |
|---|---|---|---|---|
| EtOH (2ml/g Ery) | 81.9 | 2.4 | | 75.9 |
| EtOH/H₂O 90/10 (1.7ml/g Ery) | 82.6 | 2.6 | | 55.7 |
| Acetone (2ml/g Ery) | 83.7 | 1.4 | 50.0 | 54.1 |
| IPA (6ml/g Ery) | 85.7 | 1.1 | 61.8 | 66.8 |
| IPA (3ml/g Ery) | 87.0 | 1.1 | | 74.6 |
| IPA (3ml/g Ery) | 86.7 | 1.7 | | |
| IPA/H2O 95/5 (1.7ml/g Ery) | 82.8 | 2.8 | 73.3 | 84.5 |
| IPA/H2O 90/10 (1.2ml/g Ery) | 85.0 | 0.9 | 67.8 | 73.3 |
| IPA/H2O 90/10 (1.8ml/g Ery) | 84.6 | 2.1 | 68.4 | 78.7 |
| IPA/H2O 80/20 (1.2ml/g Ery) | 88.4 | 2.4 | 75.4 | 88.0 |
| IPA/H2O 70/30 (1.2ml/g Ery) | 83.6 | 3.9 | 72.7 | 84.9 |

Among the solvents or solvent combinations studied, acetone and ethanol produced finer crystals which slowed down the filtration step. The purity and recovery of the crystals were also less with these reactants. Isopropyl acetate was too soluble for the oxime. Straight isopropanol always resulted in insoluble residues. The data show that a combination of isopropanol and water produced the highest crystal purity and yield.

What is claimed is:

1. A process of increasing the E to Z isomeric ratio of 9-oxime erythromycin A comprising preparing the 9-oxime erythromycin A by reacting erythromycin A with hydroxylamine in the presence of isopropanol and acetic acid or formic acid.

2. The process of claim 1 wherein the catalyst is acetic acid.

3. The process of claim 1 wherein the catalyst is formic acid.

4. The process of claim 1 wherein hydroxylamine is added to a solution of erythromycin A in isopropanol to form a mixture followed by the addition of the catalyst to the mixture.

5. The process of claim 4 wherein a 50% aqueous solution of hydroxylamine is added to a mixture of erythromycin A in isopropanol followed by the addition of acetic acid.

* * * * *